United States Patent

Aoyama et al.

Patent Number: 5,821,392
Date of Patent: Oct. 13, 1998

[54] MANUFACTURING METHOD FOR 1,1,1,3,3-PENTAFLUOROPROPANE

[75] Inventors: Hirokazu Aoyama; Akinori Yamamoto; Noriaki Shibata, all of Settsu, Japan

[73] Assignee: Daikin Industries Ltd., Osaka, Japan

[21] Appl. No.: 875,923

[22] PCT Filed: Feb. 8, 1996

[86] PCT No.: PCT/JP96/00272

§ 371 Date: Aug. 11, 1997

§ 102(e) Date: Aug. 11, 1997

[87] PCT Pub. No.: WO96/25379

PCT Pub. Date: Aug. 22, 1996

[30] Foreign Application Priority Data

Feb. 13, 1995 [JP] Japan ................................. 7-049055

[51] Int. Cl.⁶ .................................................. C07C 19/08
[52] U.S. Cl. ............................................................ 570/176
[58] Field of Search ...................................... 570/123, 176

[56] References Cited

U.S. PATENT DOCUMENTS 5,426,253  6/1995  Morikawa et al. ..................... 570/176

FOREIGN PATENT DOCUMENTS

| 0 611 744 A1 | 8/1994 | European Pat. Off. |
| 1-242536 | 9/1989 | Japan |
| 2-218627 | 8/1990 | Japan |
| 5-213793 | 8/1993 | Japan |
| 6-256235 | 9/1994 | Japan |

*Primary Examiner*—Amelia Owens
*Attorney, Agent, or Firm*—Armstrong, Westerman, Hattori, McLeland & Naughton

[57] ABSTRACT

A manufacturing method for 1,1,1,3,3-pentafluoropropane by reducing 2,3-dichloro-1,1,1,3,3-pentafluoropropane as a raw material with hydrogen under the presence of a catalyst in a gaseous phase to produce 1,1,1,3,3-pentafluoropropane where a hydrogenation catalyst is used composed of palladium and at least one kind of additional metal selected from the group of silver, gold, copper, zinc, rhenium, cobalt, nickel, iridium, ruthenium, rhodium, tantalum, niobium, molybdenum, osmium and tungsten.

9 Claims, No Drawings

MANUFACTURING METHOD FOR 1,1,1,3,3-PENTAFLUOROPROPANE

INDUSTRIAL FIELDS WHERE THE INVENTION CAN BE UTILIZED

This invention relates to a manufacturing method for a useful compound of 1,1,1,3,3-pentafluoropropane which can be subustituted for CFC and HCFC which are utilized for a cooling medium, a blowing agent or a cleaning agent.

PRIOR ART

As a manufacturing method for 1,1,1,3,3-pentafluoropropane, it is known that 2,3-dichloro-1 1,1,1,3,3-pentafluoropropane and 2,2,3-trichloro-1,1,1,3,3-pentafluoropropane as raw materials are reduced with hydrogen under the presence of a palladium catalyst carried by active carbon etc.(Japanese Patent Opening No. 256235/94).

However, this known reducing process has a weak point that the activity of palladium catalyst comes to be declined by sintering etc. because the reaction is conducted at a high temperature ranging 250° to 300° C.

OBJECTIVES OF THE INVENTION

The object of this invention is to provide a manufacturing method for obtaining useful 1,1,1,3,3 -pentafluoropropane with high yield, maintaining an activity of the catalyst to make its' lifetime longer.

THE CONSTRUCTION OF THE INVENTION

In a manufacturing process of 1,1,1,3,3-pentafluoropropane by reducing 2,3-dichloro-1,1,1,3,3-pentafluoropropane with hydrogen, as a result of closely studying a catalyst which scarcely declines the catalytic activity, the inventors found a process where the decline of catalytic avtivity by sintering etc. can be suppressed by alloying palladium and at least one kind of additional metal selected from the group of silver, gold, copper, zinc, bismuth, rhenium, cobalt, nickel, iridium, ruthenium, rhodium, tantalum, niobium, molybdenum, osmium and tungsten. This invention has thus been accomplished.

That is, the summary of this invention is in a manufacturing method for 1,1,1,3,3-pentafluoropropane in which when 2,3-dichloro-1,1,1,3,3-pentafluoropropane as a raw material is reacted with hydrogen under the presence of a catalyst in a gaseous phase to produce 1,1,1,3,3-pentafluoropropane, a hydrogenation catalyst composed of palladium and at least one kind of additional metal selected from the group of silver, gold, copper, zinc, bismuth, rhenium, cobalt, nickel, iridium, ruthenium, rhodium, tantalum, niobium, molybdenum, osmium and tungsten is used as the catalyst.

As for the process of the gas phase reaction based on the present invention, such processes as the fixed-bed vapor phase reaction and fluidized-bed vapor phase reaction etc. can be used.

The hydrogenation catalyst used in the present invention is composed of palladium and specific additional metal, and they can be an alloy or an oxide thereof. The specific additional metal is at least one kind of metal selected from the group of silver, gold, copper, zinc, bismuth, rhenium, cobalt, nickel, iridium, ruthenium, rhodium, tantalum, niobium, molybdenum, osmium and tungsten.

A ratio of the specific additional metal to palladium can be applied ranging from 0.01 to 100% by weight, and preferably from 0.1 to 30% by weight.

As a preparing method for the hydrogenation catalyst in the present invention, various kind of known preparing method for the hydrogenation catalyst can be applied, for example, an aqueous solution of a salt containing of a catalytic component or the aqueous solution added by hydrochloric acid is impregnated in a carrier before dried and reduced with hydrogen etc.

As a carrier of the hydrogenation catalyst used in the present invention, at least one kind of the carrier selected from active carbon, alumina, silica gel, titanium oxide and zirconia can be used. Particularly, active carbon is preferable because 1,1,1,3,3-pentafluoropropane as the objective can be obtained with high selectivity.

Though the particle size of the carrier has little effect on the reaction, it is preferably from 0.1 to 100 mm.

As for the catalyst concentration on the carrier, though a wide range from 0.05 to 30% by weight can be used, the concentration from 0.5 to 5% by weight is usually recommended.

The reaction temperature in the present invention is usually ranging from 100° to 350° C., preferably from 200° to 300° C.

As the reduction reaction of 2,3-dichloro-1,1,1,3,3-pentafluoroprpopane with hydrogen based on the present invention, the ratio of hydrogen to the raw material can be changed widely as long as the hydrogen amount is not less than stoichiometric amount (or at least the stoichiometric amount) for 2,3-dichloro-1,1,1,3,3-pentafluoroprpopane. However, the hydrogenation is usually carried out by using hydrogen in an amount of 1.5 to 3 times as large as stoichiometric amount. To the total mole of the starting material, a considerably excessive moles of hydrogen compared with the stoichiometric amount, for example, 10 or more times the stoichiometric amount, can be used.

The reaction pressure is not restricted particularly. Though the reaction can be carried out under pressure, reduced pressure or normal pressure, it is preferable to carry out the reaction under pressure or normal pressure, because the appartus may be complicated for reduced pressure.

The contact time is usually from 0.1 to 300 seconds, preferably from 1 to 30 seconds.

In the present invention, 2,3-dichloro-1,1,1,3,3-pentafluoroprpopane as a raw material is known compound, and this can be produced by fluorination of perchloropropene (refer to E. T. McBEE, ANTHONY TRUCHAN, R. O. BOLT, J.Amer.Chem. Soc., vol.170, 2023–2024(1948)).

THE POSSIBILITY OF UTILIZING THE INVENTION IN INDUSTRY

According to the present invention, in a method of manufacturing 1,1,1,3,3-pentafluoropropane by reducing 2,3-dichloro-1,1,1,3,3-pentafluoropropane as a raw material with hydrogen under the presence of a catalyst in a-gaseous phase, the hydrogenation catalyst having a long lifetime comprising palladium and additional metal which is at least one selected from the group of silver, gold, copper, zinc, bismuth, rhenium, cobalt, nickel, iridium, ruthenium, rhodium, tantalum, niobium, molybdenum, osmium and tungsten is used as the catalyst. Consequently, usuful 1,1,1,3,3 -pentafluoropropane can be produced with high yield. In addition, the cost required for the catalyst or for exchanging it can be cut down, to provide an economically advantageous manufacturing method.

EMBODIMENTS

This invention will be explained in more detail through the following examples.

<Preparation Example 1>

An acidic aqueous solution added by hydrochloric acid, containing palladium chloride and iridium chloride having the proportional ratio of the respective metal components of 90:10 by weight which were dissolved in the solution at 3% by total weight of the metal components to the weight of active carbon, was impregnated into an active carbon. After water was removed at reduced pressure, it was further dried at 120° C. for 10 hours. Next, a SUS-316 reactor tube was filled up with the catalyst, and after it was further dried at 250° C. for 5 hours while passing nitrogen gas, hydrogen was introduced while keeping this temperature for 5 hours to conduct the reduction of the catalyst.

<Preparation Example 2>

An acidic solution added by hydrochloric acid, containing palladium chloride and osmium chloride having the propotional ratio of the respective metal components of 90:10 by weight which were dissolved in the solution at 3% by total weight of the metal components to the weight of active carbon, was impregnated into an active carbon. After water was removed at reduced pressure, it was further dried at 120° C. for 10 hours. Next, a SUS-316 reactor tube was filled up with the catalyst, and after it was further dried at 250° C. for 5 hours while passing nitrogen gas, hydrogen was introduced while keeping this temperature for 5 hours to conduct the reduction of the catalyst.

<Preparation Example 3>

An acidic solution added by hydrochloric acid, containing palladium chloride and nickel chloride having the propotional ratio of the respective metal components of 80:20 by weight which were dissolved in the solution at 2% by total weight of the metal components to the weight of active carbon, was impregnated into an active carbon. After water was removed at reduced pressure, it was further dried at 120° C. for 10 hours. Next, a SUS-316 reactor tube was filled up with the catalyst, and after it was further dried at 250° C. for 5 hours while passing nitrogen gas, hydrogen was introduced while keeping this temperature for 5 hours to conduct the reduction of the catalyst.

<Preparation Example 4>

An acidic solution added by hydrochloric acid, containing palladium chloride and rhodium chloride having the proportional ratio of the respective metal components of 95:5 by weight which were dissolved in the solution at 3% by total weight of the metal components to the weight of active carbon, was impregnated into an active carbon. After water was removed at reduced pressure, it was further dried at 120° C. for 10 hours. Next, a SUS-316 reactor tube was filled up with the catalyst, and after it was further dried at 250° C. for 5 hours while passing nitrogen gas, hydrogen was introduced while keeping this temperature for 5 hours to conduct the reduction of the catalyst.

<Preparation Example 5>

A catalyst of palladium carried on active carbon at 3% concentration was soaked into an aqueous solution in which silver nitrate was dissolved so that the concentration of silver as the metal component was 10% by weight to palladium. After water was removed at reduced pressure, it was further dried at 120° C. for 5 hours. Next, a SUS-316 reactor tube was filled up with the catalyst, and after it was further dried at 300° C. for 5 hours while passing nitrogen gas, hydrogen was introduced while keeping this temperature for 5 hours to conduct the reduction of the. catalyst.

<Preparation Example 6>

A catalyst of palladium carried on active carbon at 2% concentration was soaked into an aqueous solution in which potassium molybdate was dissolved so that the concentration of molybdenum as the metal component was 5% by weight to palladium. After water was removed at reduced pressure, it was further dried at 120° C. for 5 hours. Next, a SUS-316 reactor tube was filled up with the catalyst, and after it was further dried at 300° C. for 5 hours while passing nitrogen gas, hydrogen was introduced while keeping this temperature for 5 hours to conduct the reduction of the catalyst.

<Preparation Example 7>

A catalyst of palladium carried on active carbon at 3% concentration was soaked into an aqueous solution in which potassium tungstate was dissolved so that the concentration of tungsten as the metal component was 10% by weight to palladium. After water was removed at reduced pressure, it was further dried at 120° C. for 5 hours. Next, a SUS-316 reactor tube was filled up with the catalyst, and after it was further dried at 300° C. for 5 hours while passing nitrogen gas, hydrogen was introduced while keeping this temperature for 5 hours to conduct the reduction of the catalyst.

Examples 1–7

Each SUS-316 reactor tube having 7 mm inside diameter and 150 mm long was filled respectively with 2.5 cc of the catalyst obtained in the above each Preparation Example. The reactor was heated to 250° C. in an electric furnace while passing nitrogen gas. After the temperature reached a given level, 2,3-dichloro-1,1,1,3,3-pentafluoropropane was introduced into the reactor at the rate of 1.0 cc/min with hydrogen at the rate of 10 cc/min. The reaction temperature was kept at 250° C. The produced gas was washed with water and then analyzed by gas chromatography. The results are shown in the following Table 1.

Comparison Example

The same reactor as used in Examples 1–7 was filled with 2.3 cc of a palladium catalyst carried on active carbon. The reactor was heated to 180° C. in an electric furnace while passing nitrogen gas. After the temperature reached a given level, 2,3-dichloro-1,1,1,3,3-pentafluoropropane was introduced into the reactor at the rate of 2.6 cc/min with hydrogen at the rate of 10 cc/min. The reaction temperature was kept at 180° C. The produced gas was washed with water and then analyzed by gas chromatography. The result is shown in the following Table 1, too.

TABLE 1

| | | Yield (%) of HFC-245fa* | |
| --- | --- | --- | --- |
| | | After 10 hours | After 500 hours |
| Example 1 | (Pd + Ir) of Preparation Example 1 | 89 | 88 |
| Example 2 | (Pd + Os) of Preparation Example 2 | 89 | 87 |
| Example 3 | (Pd + Ni) of Preparation Example 3 | 92 | 91 |
| Example 4 | (Pd + Rh) of Preparation Example 4 | 96 | 94 |
| Example 5 | (Pd + Ag) of Preparation Example 5 | 95 | 94 |
| Example 6 | (Pd + Mo) of Preparation Example 6 | 90 | 89 |
| Example 7 | (Pd + W) of Preparation Example 7 | 89 | 87 |
| Comparison Example | Pd | 95 | 64 |

*HFC-245fa: 1,1,1,3,3-pentafluoropropane

This result apparently shows that the hydrogenation catalyst based on the present invention can keep the activity for long time, and the objective can be obtained with high yield. To the contrary, the catalyst activity in Comparison Example is considerably declined when being used for long time.

We claim:

1. A manufacturing method for 1,1,1,3,3-pentafluoropropane in which 2,3-dichloro-1,1,1,3,3-pentafluoropropane as a raw material is reacted with hydrogen under the presence of a catalyst in a gaseous phase to produce 1,1,1,3,3-pentafluoropropane, wherein said catalyst is a hydrogenation catalyst composed of palladium and at least one kind of additional metal selected from the group consisting of silver, gold, copper, zinc, bismuth, rhenium, cobalt, nickel, iridium, ruthenium, rhodium, tantalum, niobium, molybdenum, osmium and tungsten.

2. A manufacturing method as defined by claim 1, where the hydrogenation catalyst is an alloy or an oxide thereof composed of palladium and said additional metal.

3. A manufacturing method as defined by claim 2, where a ratio of said additional metal to palladium is 0.01 to 100% by weight.

4. A manufacturing method as defined by claim 3, where a ratio of said additional metal to palladium is 0.1 to 30% by weight.

5. A manufacturing method as defined by any of claims 1 to 4, where said hydrogenation catalyst is carried by at least one kind of carrier selected from the group consisting of active carbon, alumina, silica gel, titanium oxide and zirconia.

6. A manufacturing method as defined by claim 5, where the hydrogenation catalyst is carried by active carbon as a carrier.

7. A manufacturing method as defined by claim 5 or 6, where a concentration of said hydrogenation catalyst carried on the carrier, which is an alloy or an oxide thereof composed of palladium and said additional metal, is 0.05 to 30% by weight.

8. A manufacturing method as defined by any of claims 1 to 4, where an amount of hydrogen is used in at least a stoichiometric amount for 2,3-dichloro-1,1,1,3,3-pentafluoropropane.

9. A manufacturing method as defined by any of claims 1 to 4, where the reaction is conducted at the temperature ranging from 100° to 350° C.

* * * * *